United States Patent [19]
Marx

[11] Patent Number: 5,876,363
[45] Date of Patent: Mar. 2, 1999

[54] DYNAMIC OUTRIGGER SYSTEM WITH DORSAL AND VOLAR CONFIGURATIONS

[76] Inventor: Ralph H. Marx, 1320 Roadrunner Ridge, Wickenberg, Ariz. 85390

[21] Appl. No.: 972,204

[22] Filed: Nov. 17, 1997

[51] Int. Cl.$^6$ .................................. A61F 5/00; A61H 1/00
[52] U.S. Cl. .................................................. 602/21; 601/40
[58] Field of Search ............................ 602/5, 6, 20, 21, 602/22; 128/878, 879, 880; 482/47, 48; 601/40

[56] References Cited

U.S. PATENT DOCUMENTS

| | | | |
|---|---|---|---|
| 897,471 | 9/1908 | Loyola | 482/48 |
| 2,520,035 | 8/1950 | Goldberg | 602/21 |
| 2,863,449 | 12/1958 | Spencer | 602/21 |
| 4,602,620 | 7/1986 | Marx | 128/77 |
| 4,949,711 | 8/1990 | Gyovai et al. | 602/21 |
| 5,538,488 | 7/1996 | Villepigue | 482/47 |

*Primary Examiner*—Richard J. Apley
*Assistant Examiner*—Denise Pothier
*Attorney, Agent, or Firm*—Warren F. B. Lindsley

[57] ABSTRACT

An outrigger system for use with a custom fit splint to achieve precise alignment of dynamic splint forces following traumatic injury, disease or surgery of the hand.

5 Claims, 3 Drawing Sheets

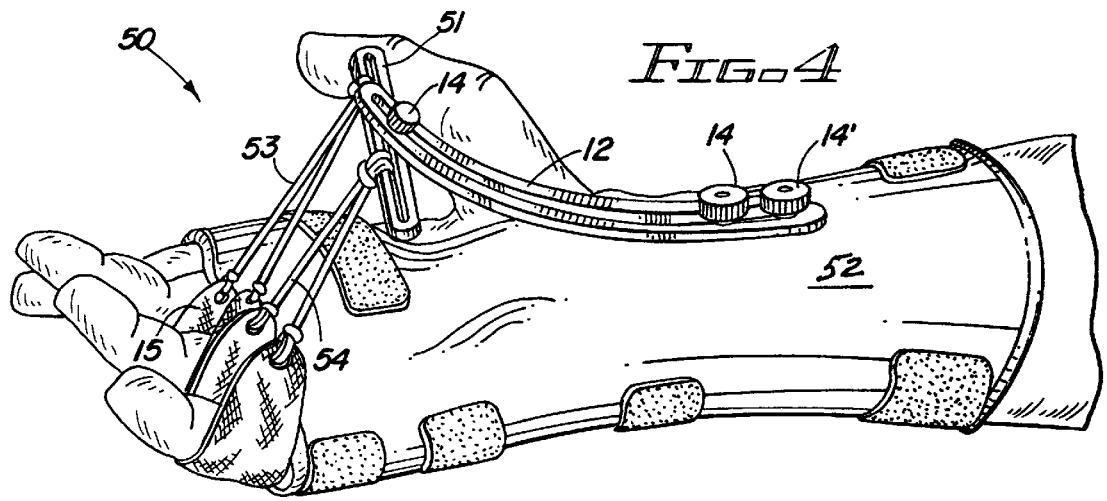
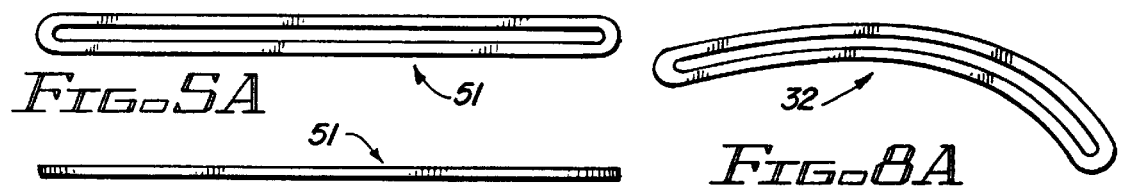
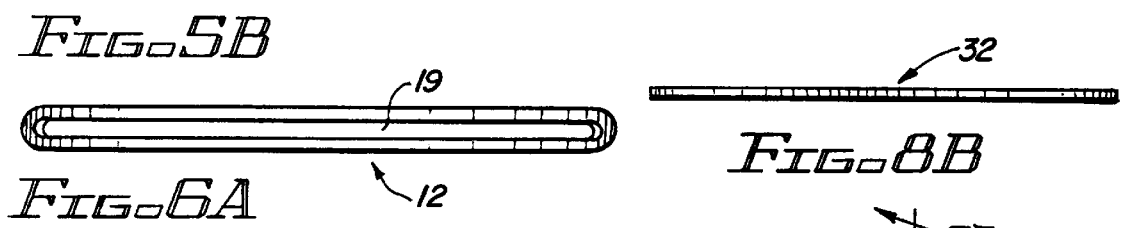
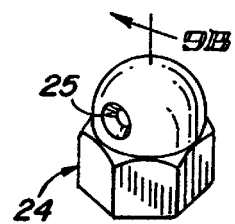
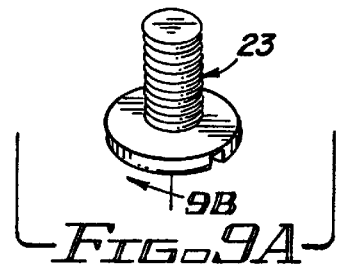
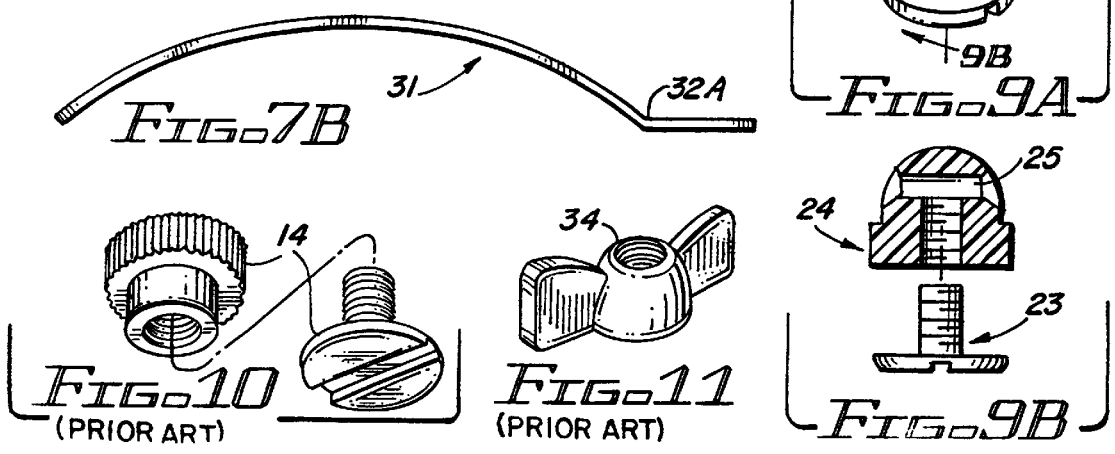
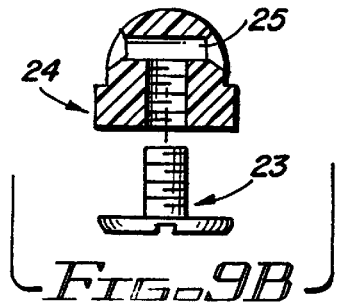

DYNAMIC OUTRIGGER SYSTEM WITH DORSAL AND VOLAR CONFIGURATIONS

BACKGROUND OF THE INVENTION

Splints are commonly used in the rehabilitation of the hand following traumatic injury, disease or surgery. Dynamic splints, those which apply traction force to the digit(s) are used to:

1. Assist motion in the weakened or paralyzed part of the hand;
2. Guide motion and maintain proper alignment of the injured/repaired part of the hand; and/or
3. Provide prolonged stretch to increase joint range of motion.

DESCRIPTION OF THE PRIOR ART

U.S. Pat. No. 4,602,620, issued to the applicant of this invention, disclosed improvements over the prior art in the form of a prefabricated dynamic extension or outrigger which is used with custom fit, thermoplastic dorsal wrist splints to meet the needs for precise alignment of dynamic splint forces following implant resection arthroplasties of the metacarpophalangeal joints. This device, which is known as the Phoenix outrigger, comprised the first known low profile outrigger means with finger metacarpophalangeal joint extension assists that can be easily and repeatedly adjusted after installation to accommodate changes in the hand during recovery.

The above disclosed device i. e. the Phoenix Outrigger, as well as the prior art devices that preceded it are lacking in a number of ways. They are typically constructed by physicians and therapists for individual patients and are generally made of wire or thermoplastics.

The Pope brace (aka Swanson brace) is a prefabricated outrigger but its use is limited to the single purpose of high-profile dynamic extension splinting. It does not employ interchangeable parts.

The SCOMAC system (manufactured by the Scomac Corporation) does offer interchangeable parts, but the parts can only be used for low profile designs and cannot be used for radially based outriggers. The SCOMAC attachments and their adjustments require the use of tools (small hex wrench and screw driver). Additionally, the open design of the SCOMAC pulley does not prevent dislocation of the low friction line in extension splinting.

The Phoenix Outrigger is limited to dorsal application for dynamic extension splinting at the level of the metacarpophalangeal joint. The angle of pull of the traction is adjusted by rotation of the wheel and is limited to a ¾ inch range. The Phoenix Single Outrigger may be used for either dorsal or volar attachment but is similarly limited in range of adjustment.

SUMMARY OF THE INVENTION

While each of the prior art devices is thus seen to offer one or more of the desired capabilities or features, none of them is found to incorporate all of the features one would like to see in an ideal dynamic outrigger system.

It is, therefore, one object of the present invention to provide a new and improved dynamic outrigger system.

Another object of this invention is to provide a standard set of parts for use in such a system whereby any of the various types of outriggers encompassed by the system may be constructed from the standard set of parts.

A further object of this invention is to provide such an outrigger system which allows dorsal, radial or volar application.

A still further object of this invention is to provide such an outrigger system which allows direction of force to any digital joint level.

A still further object of this invention is to provide such an outrigger system with a capability for controlling traction forces to single or multiple digits.

A still further object of this indention is to provide such an outrigger system with a capability for following the anatomical curves of the hand and the arc of motion of the digits.

A still further object of this invention is to provide such an improved outrigger system that employs interchangeable and adjustable parts as well as bases which may be bent by the physician or therapist to meet individual requirements.

Yet another object of this invention is to provide such an improved outrigger system that includes constructions of both high and low profile dynamic splints.

BRIEF DESCRIPTION OF THE DRAWINGS

The present invention may be more readily described with reference to the accompanying drawings, in which:

FIG. 4 is a perspective view showing a volar application of the outrigger system of the invention in which one digit is subjected to metacarpophalangeal flexion and another digit is subjected to proximal interphalangeal flexion;

FIGS. 5A and 5B show plan and side views of a first slotted cross-arm which serves as a first member of a set of standard parts comprising the outrigger system of the invention;

FIGS. 6A and 6B show plan and side views of a first slotted extension arm which serves as another member of a set of standard parts comprising the outrigger system of the invention;

FIGS. 7A and 7B show plan and side views of a second slotted extension arm serving as another member of a set of standard parts comprising the outrigger system of the invention;

FIGS. 8A and 8B show plan and side views of a second slotted cross-arm serving as another member of a set of standard parts comprising the outrigger system of the invention;

FIG. 9A is a perspective view of a screw and mating tension line guide comprising another member of the set of standard parts;

FIG. 9B is a cross-sectional view of the screw and mating tension line guide of FIG. 9A;

FIG. 10 is a perspective view of another member of the set of standard parts in the form of a screw and a mating thumb nut employed for attaching cross-arms to extension arms and for attaching extension arms to wrist or hand splints;

FIG. 11 shows a wing nut that may be employed in place of the thumb nut of FIG. 10;

DESCRIPTION OF THE PREFERRED EMBODIMENT

Referring more particularly to the drawings by characters of reference, FIGS. 1 through 4 show four different applications of the improved dynamic outrigger system.

Figure 1:
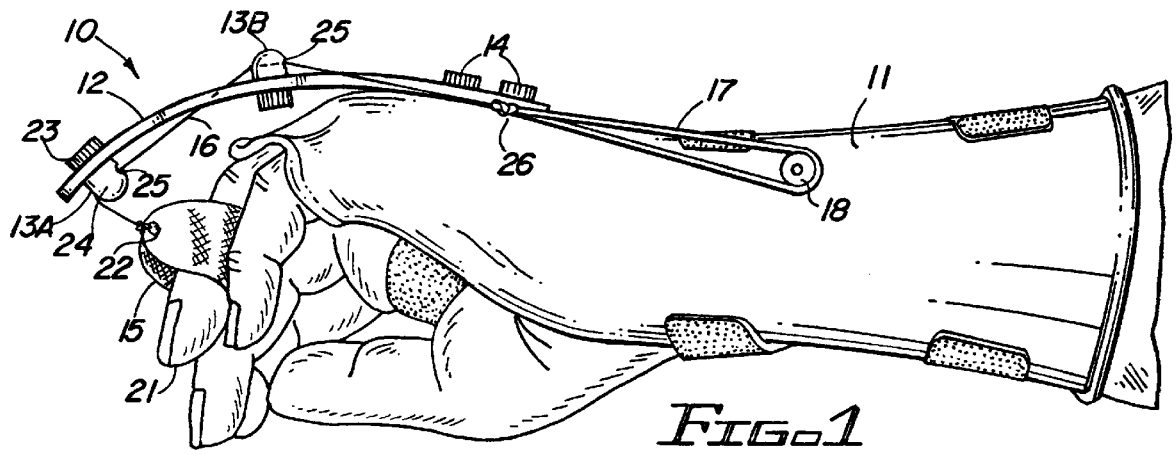
FIG. 1 is a perspective view showing a dorsal application of the outrigger system of the invention in which a single digit is subjected to proximal interphalangeal extension.

FIG. 1 shows its application on an ulnar gutter splint to provide proximal interphalangeal extension to a single digit, in this case the ring finger.

The outrigger 10 is mounted upon a thermo-plastic cast or splint 11 that covers the back of the hand and the proximal phalanges of the four fingers.

Figure 12:
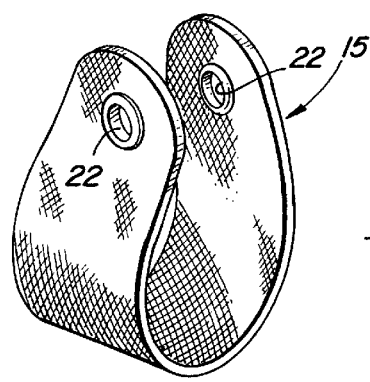
FIG. 12 is a perspective view of another member of the set of standard parts in the form of a finger cuff or sling.

The outrigger 10 comprises an extension arm 12, two tension line guides, 13A and 13B, two attachment screws and mating thumb nuts 14 of the type shown in FIG. 10, a finger cuff 15, also shown in FIG. 12, a tension line 16 such as, for example, a 20 lb. test monofilament line, elastic line, dental floss or rubber band 17, and a tension line/elastic band anchor 18.

The extension arm 12 in FIGS. 6A and 6B is slotted as shown in the plan view of FIG. 6A and curved or cylindrical as viewed from the side in FIG. 6B. Arm 12 is secured to splint 11 at its proximal end by means of the two screws and thumb nuts 14, the screws passing through the splint 11 and through the slot 19 of arm 12. In its mounting position arm 12 is aligned with finger 21 that is undergoing extension, and the curvature of arm 12 follows the downward curvature of the fingers when in partial flexion with the distal end of arm 12 passing over the center of the proximal-distal phalanx.

The finger cuff 15 as shown in FIG. 12 is made of leather or similar material in the form of a strap that is punctured or pierced at both ends 22 to receive the end of tension line 16 shown in FIG. 1.

Figure 13:
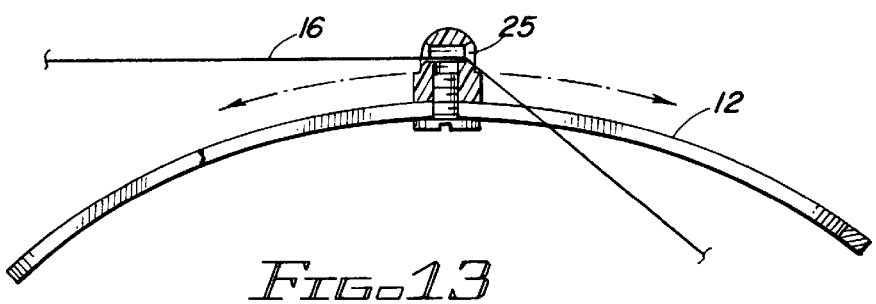
FIG. 13 illustrates the assembly of a tension line guide to a cross-arm.

Tension line guide 13A of FIG. 1 is mounted to arm 12 at a position directly over the center of the proximal-distal phalanx, the screw 23 of guide 13A passing through slot 19 from above arm 12 and a guide nut 24 engaging screw 23 from below arm 12. A transverse passage 25 through the head of guide 13A is aligned with finger 21 and with arm 12. The mounting of guide nut 24 and screw 23 to extension arm 12 is more clearly illustrated in FIG. 13.

The second tension line guide 13B of FIG. 1 is similarly mounted upon arm 12 at a position approximately midway between guide 13B and the attachment thumb nuts 14. In this case, however, the guide nut is positioned above arm 12 with passage 25 again aligned with arm 12.

The tension line 16 passes from its attachment to finger cuff 15 through the transverse passage 25 of guide 13A, through slot 19 of arm 12 and through the transverse passage 25 of guide 13B to a point 26 where its end is attached to the distal end of elastic line 17. As indicated earlier, the proximal end of elastic line 17 is attached to screw and thumb nut 18. The relative lengths of tension line 16 and elastic line 17 are adjusted to obtain the desired tension level that is to be applied to finger 21.

It will be noted that slotted arm 12 provides a wide range of adjustment for the accommodation of different hand sizes. This wide range of adjustment also permits treatment of any one of the three finger joints metacarpophalangeal (MP), proximal interphalangeal (PIP) or distal interphalangeal (DIP) using the same set of standard parts.

Figure 2:
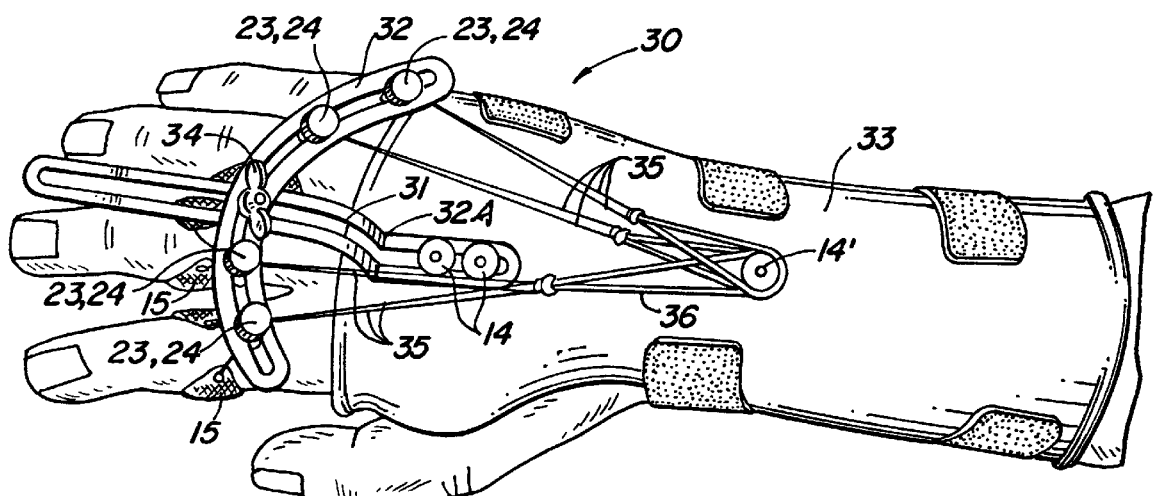
FIG. 2 is a perspective view showing a dorsal application of the outrigger system of the invention in which multiple digits are subjected to metacarpophalangeal extension.

The forearm based dorsal configuration 30 of FIG. 2 employs the extension arm 31 of FIGS. 7A and 7B and the slotted cross-arm 32 of FIGS. 8A and 8B in an arrangement that applies metacarpophalangeal extension to all four digits. The curve approximates anatomical arch formed by relative lengths of the metacarpals of the hand.

The slotted extension arm 31 of FIGS. 2, 7A and 7B has its proximal end bent at point 32A in order to achieve the higher profile that is needed for metacarpophalangeal extension. The extension arm 31 is curved from point 32A forward to follow the curvature of the partially flexed digits and it is flat from point 32A rearward to the proximal end of arm 31.

The curved and slotted cross-arm 32, as shown in FIGS. 8A and 8B is employed in the configuration of FIG. 2 to provide points of support for all four digits. As shown in FIGS. 8A and 8B the cross-arm 32 is curved as seen in the plan view of FIG. 8A and flat as seen from the side in FIG. 8B. The curved form of FIG. 8A is intended to follow the arc that is defined by the) centers of the four proximal phalanges.

As shown in FIG. 2, the flat portion of arm 31 is secured at a centered point over the metacarpal area of the hand to a cast or splint 33 that covers the dorsal metacarpal area of the hand and extends over a portion of the forearm. The -extension arm 31 is again secured to splint 33 using the screws and thumb nuts 14.

The cross-arm 32 is transversely attached, approximately at its center to extension arm 31 at an angle and a location relative to extension arm 31 that aligns the curved cross-arm 32 with the centers of the four proximal phalanges, the curvature of the cross-arm following that of the four phalanges. In this case, a screw and a wing nut 34 as shown in FIG. 11 are employed to secure arm 32 to arm 31.

Figure 14:
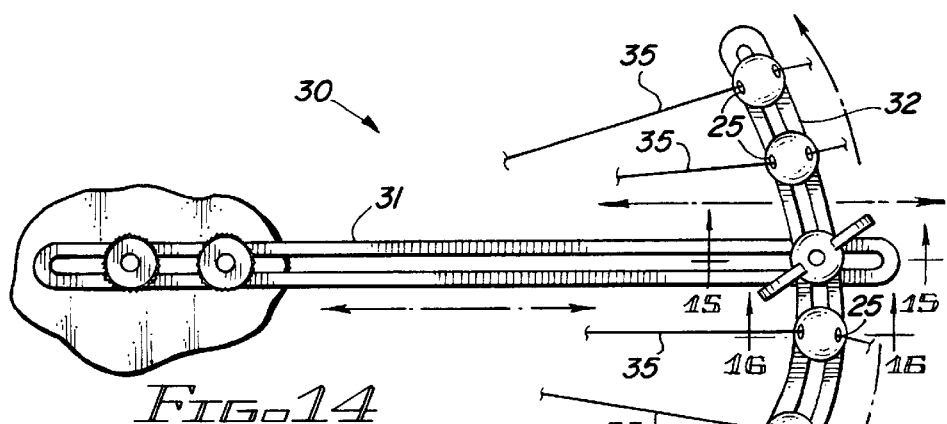
FIG. 14 is a plan view of the outrigger of FIG. 2.
Figure 15:
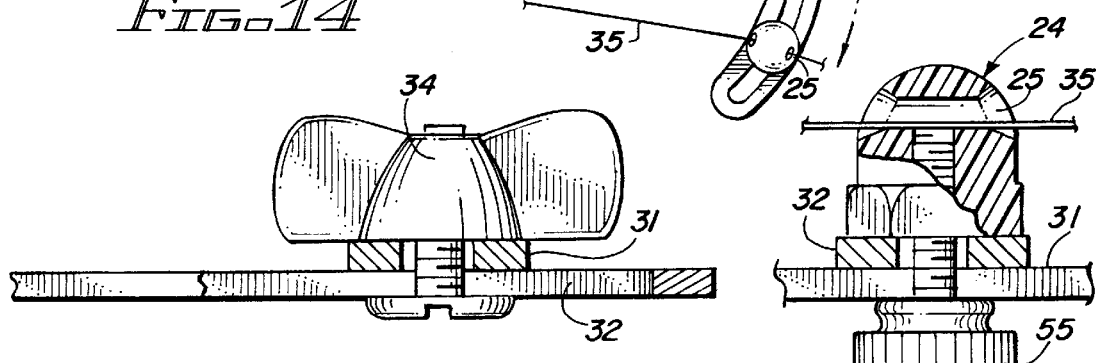
FIG. 15 is a cross-sectional view taken along line 15—15 of FIG. 14.
Figure 16:
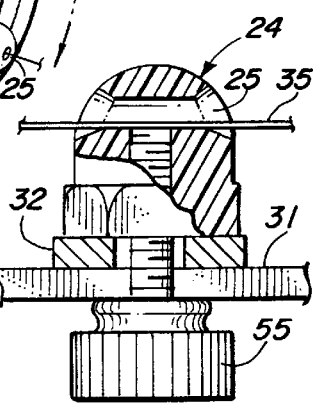
FIG. 16 is a cross-sectional view taken along line 16—16 of FIG. 14.

Four sets of the screw 23 and guide nut 24 are positioned along the length of cross-arm 32 at the appropriate locations for guiding the tension lines 35 from the four slings or cuffs 15 to the attached rubber bands 36 which, in turn, are attached to a screw, thumb nut anchor 14' that is secured to splint 33 at a point located over the middle of the hand. In this case, a single guide nut serves adequately for each digit because the higher profile leaves a more spacious opening through which the tension lines may pass. The mounting and orientation of the cross-arm 32 relative to extension arm 31 and the orientation of the transverse passage 25 are more clearly shown in FIGS. 14, 15 and 16.

Again it will be noted that the slotted extension arm and the slotted cross-arm permit a wide range of adjustment so that a single set of standard parts will accommodate a wide range of hand and digit dimensions.

Figure 3:
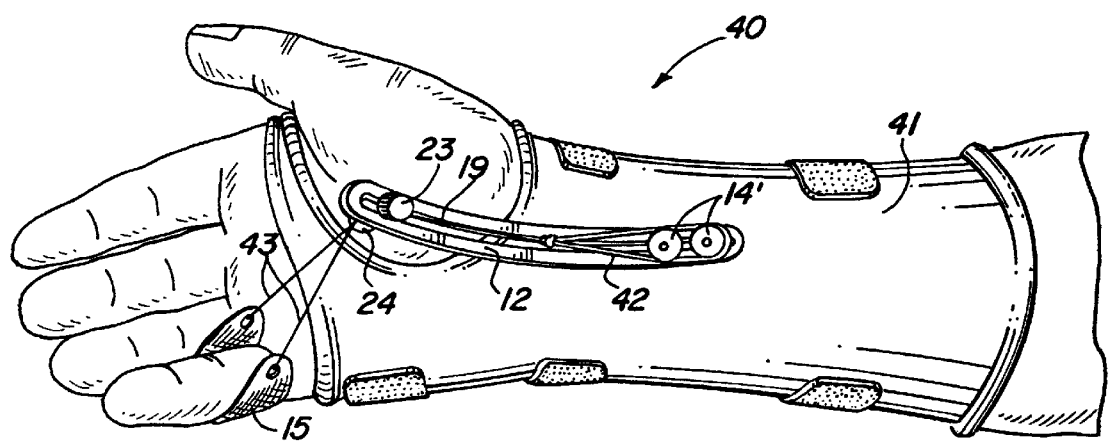
FIG. 3 is a perspective view showing a volar application of the outrigger system of the invention in which a single digit is subjected to metacarpophalangeal flexion.

The volar, forearm-based splint 40 of FIG. 3 employs the same extension arm 12 that was employed in the dorsal configuration of FIG. 1. Two of the same screw and thumb nut pairs 14, 14' serve as anchors for the proximal end of arm 12 which is secured to the wrist/forearm splint 41.

The same screw and guide nut assembly 23, 24 that was employed in the configurations of FIGS. 1 and 2 is employed in outrigger 40. As shown in FIG. 3, the distal end of arm 12 extends over the palm of the hand to a point over the proximal phalanx where the screw and guide nut assembly are positioned with the guide nut facing the volar surface of the little finger.

The elastic line 42 has its proximal end anchored to the screw, thumb nut 14' and its distal end is secured to the tension lines 43 which pass through the slot 19 of arm 12, through the transverse passage 25 of guide nut 24, to the attachment holes of the finger cuff 15.

It should be noted that with appropriate mounting orientation the outrigger 40 of FIG. 3 could be made to apply flexion to any one of the four digits.

The volar outrigger 50 of FIG. 4 employs the same extension arm 12 that was employed in the outriggers of FIGS. 1 and 3, together with two of the screw and thumb nut pairs 14, 14', two finger cuffs 15 and one additional standard part in the form of the straight, slotted cross-arm 51 of FIGS. 5A and 5B.

Extension arm 12 is again mounted by means of the screw-thumb nuts 14, 14' to the hand and wrist splint 52 in nearly the same position as it was mounted in the configuration of FIG. 3.

The splint 52 extends just short of the PIP joints to -enable PIP flexion.

The straight cross-arm 51 is secured at its center to the distal end of arm 12 using a screw-thumb nut pair 14. In its transverse orientation relative to arm 12, the cross-arm 51 provides appropriate attachment points for the rubber bands 53, 54 which are attached as shown to the finger cuffs 15.

The finger cuffs 15 are held by the rubber bands in their positions around the two fingers undergoing PIP flexion.

It will be noted that the outrigger 50 is readily adaptable for the application of radial flexion. To apply a radial vector to the little finger, for example, the rubber band attached to the cuff of the little finger would be attached at the opposite end of cross-arm 51.

The improved dynamic outrigger system of the invention is thus shown to comprise a versatile set of standard parts that may readily be assembled to form any of a number of outrigger configurations as needed for MP, IP or DIP flexion or extension.

In accordance with the stated objects of the invention, the outrigger system of the invention offers important improvements over the prior art with its multi-purpose, interchangeable parts, its very limited need for tools, its adjustability for conformance to different hand and finger dimensions and its adaptability to dorsal and volar, high profile and low profile and hand-based as well as forearm based configurations.

Although but a few embodiments of the invention have been illustrated and described, it will be apparent to those skilled in the art that various changes and modifications may be made therein without departing from the spirit of the invention or from the scope of the appended claims.

What is claimed is:

1. An outrigger system for use with a splint for precise alignment of dynamic splint forces in flexion or extension and through the arc of motion of the digits of a hand comprising:

an outrigger comprising a low profile narrow elongated frame member having two spaced apart ends, one end securable to the splint, said frame member being distorted along its length to position its ends in different parallel planes, an arcuate portion extending transverse of and connected to said frame member and having a slot along its length for accommodating the differences in length of the metacarpals of the hand, a plurality of guide nuts being positioned on said portion one adapted to be juxtapositioned above each phalange of the hand on which the outrigger is mounted, each of said guide nuts being adjustably positioned radially of and longitudinally along the slot of said portion, and means for controlling the position of a phalange having a tension line with a first and second end, said first end adapted to attach to an associated phalange and the second end attached to the splint.

2. The combination set forth in claim 1 wherein:

said transverse portion is curved along its length to follow the arc that is defined by the center of the four proximal phalanges.

3. The combination set forth in claim 1 wherein:

said frame member is curved over a portion of its length and flat over the remainder of its length, said flat portion being securable to the splint and said curved portion adapted to extend over the dorsal side of the phalanges and attached to a wing nut, whereby the curved portion accommodates an anatomical arch formed by the metacarpals of the hand to maintain an angle of pull to the phalanges.

4. The combination set forth in claim 1 wherein:

said transverse portion is curved as seen in a plan view and straight as viewed from the side, said curved transverse portion frame being for dorsal outrigger configuration and the application of forces to multiple digits.

5. The combination set forth in claim 1 wherein:

said frame member is curved over its length and adapted to secure to the splint at one end thereof with the other end adapted to extend over the volar side of the phalanges and attached to an associated guide nut.

* * * * *